United States Patent [19]

Gross

[11] 4,105,793

[45] Aug. 8, 1978

[54] MULTIFUNCTIONAL ACRYLATES AS FOLIAR FUNGICIDES

[75] Inventor: Arthur L. Gross, Stockton, Calif.

[73] Assignee: Celanese Corporation, New York, N.Y.

[21] Appl. No.: 709,557

[22] Filed: Jul. 28, 1976

[51] Int. Cl.² ............................................. A01N 9/24
[52] U.S. Cl. .................................................. 424/314
[58] Field of Search ....................................... 424/314

[56] References Cited

U.S. PATENT DOCUMENTS

| | | | |
|---|---|---|---|
| 3,097,998 | 7/1963 | Miller | 424/314 |
| 3,156,612 | 11/1964 | Butler et al. | 424/314 |

FOREIGN PATENT DOCUMENTS 1,099,200  4/1955  France.

OTHER PUBLICATIONS

Bassemir et al., C.A. vol. 74 (1971) 55342w.
Moyer Safford et al., C.A. vol. 68 (1968) 22550h.
C.A., vol. 71 (1969) 13790y.

*Primary Examiner*—Allen J. Robinson

[57] ABSTRACT

Multifunctional acrylates such as pentaerythritol triacrylate for protectant control of e.g., leaf rust of wheat, late blight of tomato rice blast disease and bean rust.

13 Claims, No Drawings

MULTIFUNCTIONAL ACRYLATES AS FOLIAR FUNGICIDES

This invention relates to fungicides and, more particularly, to foliar fungicides as protectants against infestation by plant pathogens.

BACKGROUND OF THE INVENTION

Foliar fungicides i.e. chemical agents having fungicidal or fungistatic properties employed in direct application e.g. sprayed onto the foliage of plant species for control or eradication of fungal infestation are well-known. Effective mycological inhibition evidenced by differentiated chemical species is a complex function of a number of variables other than specific activity including resistance to weathering, and varying levels of phytotoxicity. In addition, ecological concern calls for consideration of the nature, and persistence of residues. Moreover, the material utilized must be easily handled, operate consistently with the spray schedule and be economical.

These requirements render the selection of effective fungicidal agents largely a function of experimentation. Many of the available materials comprise complex molecules of specific functionality, difficult or expensive to prepare, and of questioned ecological desirability.

Accordingly, it is an object of the present invention to afford effective topical agents for the control of fungal infestation including molds, mildews, rusts, yeasts and smuts, especially for protectant control in agriculture.

It is a further object to identify chemical agents and compositions for such use characterized by relatively simple chemical constitution.

U.S. Pat. No. 2,379,294 shows the use of e.g., crotonic acid or its salts and esters in the retardation of growth of microorganisms in and on food products, as a substitute for sodium benzoate. U.S. Pat. No. 2,532,579 describes bacteriostatic use of beta-acylacrylic acid species, and reports no activity of the parent acid. U.K. Pat. No. 1,314,089 refers to phenyl acrylates in anti-fungal compositions. U.S. Pat. Nos. 3,773,518 and 3,806,615 are drawn to 1,3-diols or their esters as mold inhibitors.

BRIEF DESCRIPTION OF THE INVENTION

In accordance with the present invention, there is provided a fungicidally effective composition consisting essentially of a polyol acrylate ester such as trimethylolpropane triacrylate, or pentaerythritol tetraacrylate. These compositions evidence inhibition of widely variant plant pathogens even in culture media, and may be generally used in the control of infestations in agriculture. Surprisingly, the multifunctional acrylates of the present invention may be used at relatively low concentration to provide protectant control against fungal infestation. Their lack of significant phytotoxicity to plant species and ecological acceptance render use in agriculture a matter of preference.

In general, the multifunctional polyol derivatives are acrylic acid or methacrylic acid esters of the selected polyol in which at least two hydroxy groups are esterified. Exemplary preferred compounds are ethylene glycol diacrylate, diethylene glycol diacrylate, glycerol diacrylate, glycerol triacrylate, ethylene dimethacrylate, 1,3-propanediol dimethacrylate, 1,2,4-butanetriol trimethacrylate, pentaerythritol tri- and tetra-acrylate and methacrylate, trimethylolpropane triacrylate, hexane diol diacrylate, tetraethylene glycol diacrylate, neopentyl glycol diacrylate, etc. or mixtures thereof in all proportions.

Although the multifunctional acrylates of the present invention may be applied directly to the locus for inhibition of fungal infestation in full strength, customarily the active fungicidal agent will be applied in a dilute form, as by spraying from a vehicle as a solution or dispersion comprising an inert diluent such as water or an organic solvent, e.g. isopropanol, ethylene glycol, acetone, benzene or the like.

Typically, the multifunctional acrylate will be applied prior to infestation as a protectant, although it also demonstrates effectiveness in retarding established growth.

The concentration of active fungicide will, of course, vary with the mycological species sought to be controlled and the environment, but will generally be formulated to supply a concentration of about 300 to 4800 ppm, applied to provide ¼ lb. to 4 lb./acre.

The fungicidal compositions may be applied to or compounded in or with any substrate susceptible to fungal infestation including wood, paper, leather, tobacco, paints, adhesives, textiles, cosmetics etc. but find preferred utility in agriculture and particularly, in the control of plant pathogens as by application to the foliage of growing crops, or processed agricultural products, or in the formulation of seed coatings.

The multifunctional acrylates, of course, may comprise part of a complex composition adapted for plant treatment, inclusive of one or more active biocidal agents.

DETAILED DESCRIPTION OF THE INVENTION

The foliar fungicidal compositions of the invention, consist essentially of a fungicidally effective amount of at least one polyol acrylate ester, and preferably comprise at least about 600 ppm of the ester in an inert liquid medium.

The preferred polyols are of short chain length comprising up to 10 carbon atoms. These compounds are at least bifunctional and preferably comprise two or more primary hydroxyl groups. The most preferred polyols are at least trifunctional.

The multifunctional acrylate derivatives are acrylic acid or methacrylic acid esters of the selected polyol in which at least two hydroxy groups are esterified. Most desirably, the hydroxyl groups are fully esterified. At least triesterified derivatives are preferred.

Best results have been achieved with pentaerythritol esters, and particularly systems comprising pentaerythritol triacrylate and/or tetracrylate. Also preferred are the acrylic and methacrylic acid esters of trimethylolpropane.

Mixtures in all proportions of the polyol acrylate esters may be employed, especially mixtures of esterification products of a given polyol such as pentaerythritol triacrylate and tetracrylate, or trimethylolpropane diacrylate and triacrylate.

The fungicide is conveniently employed in a form adapted to conventional agricultural spraying i.e., in an inert liquid medium. Hence, while it may be prepared and stored in an essentially pure condition, it is normally formulated with water as a vehicle in application. The active agent may be wetted or dissolved with acetone, benzene, ethylene glycol, isopropanol or the like, and dispersed or emulsified in a concentrated water system, optionally with the aid of a surfactant. The concentrate may comprise any suitable amount of active agent adapted for further dilution upon application at selected dosage levels for the topography and species being treated.

Normally, application levels at usual and customary crop densities will range from ½ lb. to 4 lb./acre, equivalent to a concentration of 600 to 4800 ppm. Obviously, more or less agent will be employed within the limits of economy and fungicidal effectiveness depending upon the severity of expected infestation, spraying conditions, etc.

The polyol acrylate esters may also be applied from a medium incorporating sticking agents in common use, or a film-former. Preferably, an emulsion of an ethylenic, especially an acrylic polymer, or polyvinyl acetate is employed.

Other adjuvants, including biocides such as herbicides, fungicides, acaricides, fertilizers; growth control agents; and the like, may be incorporated in the fungicidal compositions of the invention where desirable or convenient.

The various multifunctional acrylate species of course have variable, preferred or specific applications as for a given plant species or particular pathogen, and will accordingly be selectively applied in accordance with the skill of the artisan.

Generally speaking the present fungicidal systems are protective rather than eradicant in nature at conventional additament levels i.e., the inventive compositions are used essentially to keep the spores or mycelia of disease causing fungi from entering treated plants.

While the invention has been described hereinabove by particular reference to foliar application where its advantages are best illustrated, it is to be understood that the system is also effective as a fungicide in other conventional usages in lawns and gardens, or for agricultural crops.

The following Examples are illustrative of the present invention. The multifunctional acrylates employed were commercially available derivatives supplied by Celanese Corporation; derivatives refer to a principal acrylate constituent.

EXAMPLE I

Trimethylol propane triacrylate was tested for efficacy as a protectant in the inhibition of a range of known plant pathogens, in the following manner:

A standard amount of mycological agar (Difco Laboratories, Detroit, Mich.) was prepared according to the manufacturer's instructions, dispensed into test tubes and sterilized by autoclaving at a steam pressure of 15 psi for 15 minutes. While the tubes were maintained at a temperature of 50° C., 0.1 weight percent of trimethylolpropane triacrylate was injected into the agar with a microliter syringe and the system mixed as thoroughly as practicable.

The admixture was allowed to gel in the common slanted configuration. This procedure was repeated to provide test culture media sufficient for four replicates of each pathogen test.

The culture media were then inoculated with pathogen by application to the surface thereof, and incubated at 25°–35° C.

Trimethylol propane triacrylate proved entirely effective at these levels in inhibiting growth of *Rhizoctonia solani, Helminthosporium maydis* and *Giberella zeae* but did not control *Fusarium oxysporium.*

EXAMPLE II

Trimethylol propane trimethacrylate was tested for efficacy as a protectant in the inhibition of a range of known plant pathogens, in the same manner as Example I.

Trimethylol propane trimethacrylate proved entirely effective at these levels in inhibiting growth of *Rhizoctonia solani, Helminthosporium maydis,* was partially effective in controlling *Giberella zeae* (sparse growth) but did not control *Fusarium oxysporium.*

EXAMPLE III

Heterobusidiomycetes is a class of fungi containing many agriculturally important pathogens. Multifunctional acrylate compounds were tested for efficacy in the protectant control of leaf rust of wheat, *Puccinia recondita* var. tritici, as an organism to represent this class in competitive testing as detailed hereinafter.

Wheat plants, *Triticum vulgare,* approximately 7 to 8 days old and 4 to 5 inches tall, (in sufficient number to permit three replicates for each test, including a control) were sprayed to incipient runoff with the indicated compounds, dried, dusted with spores of *Puccinia recondita* var. tritici directly from diseased plants, and incubated at 70° F. and 95% + relative humidity.

After disease development under greenhouse conditions, disease severity (infection pressure) was determined by actual count of developed pustules on inoculated but otherwise untreated controls. Control effectiveness was determined by actual count of the number of developed pustules appearing on the respective treated plants as compared directly to developed pustules on inoculated untreated controls.

Results are set forth in the following Table.

TABLE I

| Multifunctional Acrylate[3] | Percent Control[1]/Injury[2] |
|---|---|
| Pentaerythritol tetraacrylate (1200 ppm, 1 lb./acre) | 95:0 |
| Pentaerythritol triacrylate | |
| (600 ppm, ½ lb./acre) | 100:1 |
| (1200 ppm, 1 lb./acre) | 100:1 |
| Trimethylol propane triacrylate | |
| (600 ppm, ½ lb./acre) | 100:1 |
| (1200 ppm, 1 lb./acre) | 100:1 |
| Neopentylglycol diacrylate (1200 ppm, 1 lb./acre) | 34:0 |
| Tetraethylene glycol diacrylate (1200 ppm, 1 lb./acre) | 62:0 |

[1]Percent control based upon comparison disease severity for replicated test plants to untreated controls.
[2]Plant injury on a scale of 0–10, 0 indicating no injury and 10 representing phytotoxicity.
[3]Compounds were dissolved in a system comprising 10 parts (vol.) of a stock solution composed of 1995 pts. of acetone, 4 parts of Span 85 (sorbitan trioleate) and 1 pt. of Tween 80 (polyoxyethylene sorbitan monooleate) diluted to 100 pts. with deionized water, to the indicated concentration.

1. Percent control based upon comparison disease severity for replicated test plants to untreated controls.

2. Plant injury on a scale of 0–10, 0 indicating no injury and 10 representing phytotoxicity.

3. Compounds were dissolved in a system comprising 10 parts (vol.) of a stock solution composed of 1995 pts. of acetone, 4 parts of Span 85 (sorbitan trioleate) and 1 pt. of Tween 80 (polyoxyethylene sorbitan monooleate) diluted to 100 pts. with deionized water, to the indicated concentration.

The triacrylate and tetraacrylate species were particularly effective, even at 600 ppm, with lesser control shown for the diacrylates, although utilized at 1200 ppm levels.

EXAMPLE IV

Phycomycetes is a class of fungi containing plant pathogens of agricultural importance. Multifunctional acrylate compounds were tested for protectant control of late blight of tomatoes, *Phytophthora infestans* as an organism representing this fungal class in competitive testing as detailed hereinafter.

Bonny Best tomato plants, *Lycopersicon esculentum* about 5 to 6 weeks old, in five-leaf growth stage (in sufficient number to permit three replicates for each test, including a control) were sprayed to incipient runoff with the indicated compounds, dried, spray-inoculated with a mixed sporangial and zoospore suspension of *Phytophthora infestans*, and incubated at 70° F. and 95% + relative humidity. After 40 hours, plants were removed from the incubation chamber and examined for total infection lesions of the top three leaves. Effectiveness of treatments was determined by direct comparison with inoculated controls.

Results are tabulated as follows:

TABLE II

| Multifunctional Acrylate[3] | Percent Control[1]/Injury[2] |
|---|---|
| Pentaerythritol tetraacrylate (1200 ppm, 1 lb./acre) | 92:0 |
| Pentaerythritol triacrylate (1200 ppm, 1 lb./acre) | 75:0 |
| Pentaerythritol triacrylate (600 ppm, ½ lb./acre) | 64:0 |
| Tetraethylene glycol diacrylate (1200 ppm, 1 lb./acre) | 83:0 |

1. Percent control based upon comparison disease severity replicated test plants to untreated controls.
2. Plant injury on a scale of 0–10, 0 indicating no injury and 10 representing phytotoxicity.
3. Compounds were dissolved in a system comprising 10 parts (vol.) of a stock solution composed of 1995 pts. of acetone, 4 parts of Span 85 (sorbitan trioleate) and 1 pt. of Tween 80 (polyoxyethylene sorbitan monooleate) diluted to 100 pts. with deionized water, to the indicated concentration.

Trimethylol propane triacrylate at ½ and 1 lb/acre, and neopentyl glycol diacrylate although showing an effect, did not evidence meaningful control. No phytotoxic effects were seen.

EXAMPLE V

Ascomycetes is a class of fungi containing many agriculturally important pathogens. Multifunctional acrylate species were also tested for activity as a protectant for rice blast disease, *Pyricularia oryzae*, as a representation of this fungal class.

Rice plants in fully developed second-leaf growth stage were treated in the same manner as the preceding Examples, spray inoculated with an aqueous spore suspension of *Pyricularia oryzae*, and incubated at 70° F., 95% + R.H. After 5 days disease severity (number of infection lesions) was assessed in comparison to untreated inoculated controls.

Pentaerythritol tetraacrylate, and pentaerythritol triacrylate, each at 1 lb./acre, evidenced 70% control of the disease without any evidence of phytotoxicity. Trimethylol-propane triacrylate was similarly effective (80% control) at 1 lb./acre. However, neopentylglycol diacrylate and tetraethylene glycol diacrylate were ineffective at 1 lb./acre and both trimethylpropane triacrylate and pentaerythritol triacrylate showed no disease control at ½ lb./acre. However, no phytotoxic effects were seen.

EXAMPLE VI

Ascomycetes is a class of fungi containing many agriculturally important pathogens. Multifunctional acrylate species were tested for activity as a protectant for powdery mildew of cucumber, *Erysiphe cichoracearum*, as a representation of this fungal class.

Straight-eight cucumber, *Cumcumis sativas* plants in first true leaf stage, about 14 to 18 days old were treated in the same manner as the preceding Examples. After the treated plants dried, they were placed among diseased cucumber plants, subjected to an initial spore shower by dusting with spores from diseased plants, and left undisturbed for 10 days. Effectiveness of treatment was determined by direct comparison of the average percentage leaf area infection on treated plants with the average percentage leaf area infection on untreated inoculated control.

At ½ lb./acre, applications of pentaerythritol triacrylate, trimethylolpropane triacrylate and tetraethylene glycol diacrylate were moderately effective (35, 19 and 40% control, respectively) in controlling this difficult infestation, whereas pentaerythritol tetraacrylate at 1 lb./acre although showing an effect did not evidence meaningful control, and neopentylglycol diacrylate at 1 lb./acre showed no disease control. However, no phytotoxic effects were seen.

EXAMPLE VII

Basidiomycetes is a class of fungi containing many agriculturally important pathogens. Multifunctional acrylate species were also tested for activity as a protectant for bean rust *Uromyces phaseoli typica*, as a representation of this fungal class.

Bean plants, *Phaseolus vulgaris*, in developed primary leaf stage (in sufficient number to permit three replicates for each test, including a control) were sprayed to incipient runoff with the indicated compounds (prepared as a composition of 2 lbs. of active agent, and 90 gm. of Igepal CO610, a non-ionic surfactant (nonylphenoxy polyethyleneoxy ethanol) in 1 liter of xylene) dried, spray inoculated with an aqueous urediospore suspension of *Uromyces phaseoli* (to which a trace of fine grain carborundum had been added) incubated (70° F. and 95% + R.H.) and then removed to the greenhouse for disease development.

Disease severity was determined by actual count of the number of developed pustules appearing on untreated inoculated controls. Effectiveness of treatment is determined by direct comparison of developed pustules on respective treated plants with those appearing on inoculated controls utilizing Maneb as a reference standard.

Pentaerythritol triacrylate at 1 lb./acre evidenced nearly 100% control and was nearly as effective (97%) at ½ lb./acre. Reduction of application level to ¼ lb./acre still showed 81% control, all runs being free of phytotoxic effect on the plants.

Trimethylolpropane triacrylate was nearly as effective at 1 lb./acre (91% control) but showed a more marked reduction in performance at lower levels of application (77% control at ½ lb./acre and 28% control at ¼ lb./acre.)

We claim:

1. A foliar fungicide consisting essentially of a fungicidally effective amount of a polyol acrylate ester in which at least three hydroxyl groups of the selected polyol are esterified with an acid selected from the group consisting of acrylic acid and methacrylic acid, said polyol acrylate ester being incorporated in an inert liquid medium.

2. The foliar fungicide of claim 1, wherein said polyol comprises pentaerythritol.

3. The foliar fungicide of claim 1, wherein said polyol comprises trimethylol propane.

4. A foliar fungicide consisting essentially of a fungicidally effective amount of an at least triesterified acrylate ester of pentaerythritol in an inert liquid medium.

5. A foliar fungicide consisting essentially of a fungicidally effective amount of an at least triesterified acrylate ester of trimethylolpropane in an inert liquid medium.

6. A method for the control of leaf rust of wheat comprising applying to uninfected wheat foliage an effective amount to inhibit the growth of leaf rust of a polyol acrylate ester selected from the group consisting of pentaerythritol tetraacrylate, pentaerythritol triacrylate and trimethylol propane triacrylate.

7. A method for the control of late blight of tomato comprising applying to uninfected tomato foliage an effective amount to inhibit the growth of late blight of a polyol acrylate ester selected from the group consisting of pentaerythritol triacrylate, pentaerythritol tetraacrylate and tetraethylene glycol diacrylate.

8. A method for the control of rice blast disease comprising applying to uninfected rice foliage an effective amount to inhibit the growth of rice blast of a polyol acrylate ester selected from the group consisting of pentaerythritol triacrylate, pentaerythritol tetraacrylate and trimethylolpropane triacrylate.

9. A method for the control of bean rust comprising applying to uninfected bean foliage an effective amount to inhibit the growth of bean rust of a polyol acrylate ester selected from the group consisting of pentaerythritol triacrylate and trimethylolpropane triacrylate.

10. A method for the inhibition of fungal infestation in plants comprising treating plant foliage with from about 300 to about 4800 ppm of trimethylol propane triacrylate.

11. A method for the inhibition of fungal infestation in plants comprising treating plant foliage with from about 300 to about 4800 ppm of pentaerythritol triacrylate.

12. A method for the inhibition of fungal infestation in plants comprising treating plant foliage with from about 300 to about 4800 ppm of pentaerythritol tetraacrylate.

13. A method for the control of fungal infestation in plants comprising applying to the foliage a fungicidally effective amount of at least one acrylic acid or methacrylic acid ester of a polyol, wherein at least three hydroxyl groups of said polyol are esterified.

* * * * *